(12) United States Patent
Wempe et al.

(10) Patent No.: US 8,183,398 B2
(45) Date of Patent: May 22, 2012

(54) 5-HYDROXY-2-METHYL-4H-PYRAN-4-ONE ESTERS AS NOVEL TYROSINASE INHIBITORS

(75) Inventors: Michael Fitzpatrick Wempe, Aurora, CO (US); Jeffrey Michael Clauson, Johnson City, TN (US); Liu Deng, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 18 days.

(21) Appl. No.: 12/755,812

(22) Filed: Apr. 7, 2010

(65) Prior Publication Data

US 2010/0216873 A1 Aug. 26, 2010

Related U.S. Application Data

(63) Continuation-in-part of application No. 12/036,358, filed on Feb. 25, 2008.

(51) Int. Cl.
*C07D 309/40* (2006.01)
*A61K 8/49* (2006.01)
*A61K 31/351* (2006.01)

(52) U.S. Cl. .................... 549/417; 514/460; 424/62
(58) Field of Classification Search .............. 549/417; 514/460
See application file for complete search history.

(56) References Cited

U.S. PATENT DOCUMENTS 4,369,174 A * 1/1983 Nagai et al. ............... 424/62

FOREIGN PATENT DOCUMENTS

| JP | 57-134409 A | | 8/1982 |
| JP | 57 134409 A | * | 8/1982 |
| JP | 57-137394 A | | 8/1982 |
| JP | 4-036217 A | | 2/1992 |

OTHER PUBLICATIONS

Beelik et al, Canadian J. of Chem. 33,p. 1361-1374 (1955).*

Ichimoto et al, Agr. and Biological Chem., 28(10), p. 723-727 (1964.*
Hurd et al, J. of Org. Chem., 23, p. 1276-1278 (1958).*
Burdock, George A., et al., "Evaluation of Health Aspects of Kojic Acid in Food," Regulatory Toxicology and Pharmacology, 2001, pp. 80-101, vol. 33.
Liu, Zu D., et al., "Synthesis of 2-Amido-3-hydroxypyridin-4(1$H$)-ones: Novel Iron Chelators with Enhanced pFe$^{3+}$ Values," Bioorganic & Medicinal Chemistry, 2001, pp. 563-573, vol. 9, Elsevier Science Ltd.
Zhang, Ji-Pang, et al., "Inhibitory Effects of Salicylic Acid Family Compounds on the Diphenolase Activity of Mushroom Tyrosinase," Food Chemistry, 2006, pp. 579-584, vol. 95, Elsevier Ltd.
Curto, Ernest V., et al., "Inhibitors of Mammalian Melancyte Tyrosinase: In Vitro Comparisons of Alkyl Esters of Gentisic Acid with Other Putative Inhibitors," Biochemical Pharmacology, 1999, pp. 663-672, vol. 57, Elsevier Science Inc.
Brockhaus, Manfred, et al., "Allylic Activiation in 4- and 3-O-tosylates of Hex-5-enopyranosides," Reactions of Enolic Sugar Derivatives, Liebigs Ann. Chem., 1974, pp. 1675-1683.
Notification of Transmittal of the International Search Report and the Written Opinion of the International Searching Authority, or the Declaration date of mailing May 29, 2009 received in corresponding International Patent Application No. PCT/US2009/000823.
Beelik, Andrew et al.; "Some new reactions and derivatives of jojic acid"; Canadian Journal of Chemistry; 33, 1361-74; 1955.
Ichimoto, Itsuo et al.; "Studies on kojic acid and its related .gamma.-pyrone compounds. VI. Catalytic hydrogenation of kojic acid"; Agricultural and Biological Chemicstry; 28(10); 723-7; 1964.
Hurd, Charles et al.; ".alpha.—Deoxykojic acid and some of its derivatives"; Journal of Organic Chemistry; 23; 1276-8; 1958.

* cited by examiner

*Primary Examiner* — Bernard Dentz
(74) *Attorney, Agent, or Firm* — Tammye Taylor; Jennifer R. Knight; Michael Carrier

(57) ABSTRACT

Skin brightening compositions based on esters of 5-hydroxy-2-methyl-4H-pyran-4-one. Also disclosed are methods of making the compositions as well as methods of using the compositions.

9 Claims, No Drawings

5-HYDROXY-2-METHYL-4H-PYRAN-4-ONE ESTERS AS NOVEL TYROSINASE INHIBITORS

CROSS-REFERENCE TO RELATED APPLICATIONS

This application is a continuation-in-part of application Ser. No. 12/036,358, entitled "5-Hydroxy-2-Methyl-4H-Pyran-4-One Esters as Novel Tyrosinase Inhibitors," filed on Feb. 25, 2008, the disclosure of which is incorporated herein by reference in its entirety.

FIELD OF THE INVENTION

The present invention relates to skin brightening compositions based on esters of 5-hydroxy-2-methyl-4H-pyran-4-one. Another aspect of the present invention relates to the method of making the compositions as well as methods of using the compositions.

BACKGROUND OF THE INVENTION

Skin hyperpigmentation has been directly related to the formation of melanin, a dark pigment formed via tyrosine. The initial steps in tyrosine to melanin conversion are mediated by the enzyme tyrosinase. Effective tyrosinase inhibitors may inhibit melanin formation and are used to reduce undesirable skin pigmentation (e.g. skin brightening and/or evening out skin tone and/or reducing the appearance of age spots). Currently, several tyrosinase inhibitors are used in the marketplace and include hydroquinone, kojic acid and arbutin. However, these products have various disadvantages; for example, kojic acid displays low bioavailability and thereby affords marginal efficacy.

A fungal metabolic product, kojic acid has been commonly used as a skin brightening ingredient. Kojic acid has been shown to be safe and effective for topical use (see review by Burdock et al., 2001, Regulatory Toxicology and Pharmacology 33: 80-101). Kojic acid monoesters and diesters have been described (Nagai, S.; Izumi, T., U.S. Pat. No. 4,369,174); they appear to have excellent tyrosinase-inhibiting activity so as to inhibit skin melanin formation. This inhibition can produce excellent effects in skin brightening.

Kojic acid halogenation (i.e. chloro-kojic acid, bromo-kojic acid, etc.) and subsequent reduction to afford allomaltol (5-hydroxy-2-methyl-4H-pyran-4-one) has been previously described (for example, Liu, Z. D. et al, *Bioorg. Med. Chem.* 2001, 9, 563-573). Furthermore, 5-hydroxy-2-methyl-4H-pyran-4-one has been described as a treatment for pigmentation disorders (Yamamoto, S. JP Patent 04036217), sunburn prevention (Sansei Pharmaceutical Co., JP Patent 57134409), and as an antioxidant for oils and fats (Sansei Pharmaceutical Co., JP Patent 57137394). Hence, compositions based on esters of 5-hydroxy-2-methyl-4H-pyran-4-one may reduce melanin formation and enhance the potential to provide a noticeable brightening benefit with decreased skin irritation. Other likely benefits for these esters may include the potential for sunburn prevention and usage as novel antioxidants. It is the object of this invention to provide such compounds and compositions.

SUMMARY OF THE INVENTION

An embodiment of the present invention concerns an ester represented by formula 1:

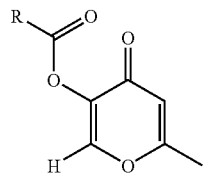

wherein R is $C_2$-$C_{24}$ alkyl, $C_2$-$C_{24}$ alkenyl, $C_4$-$C_{24}$ dienyl, $C_6$-$C_{24}$ trienyl, $C_8$-$C_{24}$ tetraenyl, or a mixture thereof, $C_6$-$C_{14}$ aryl, substituted $C_6$-$C_{14}$ aryl, substituted and unsubstituted $C_4$-$C_{20}$ heterocyclic wherein the heteroatoms are selected from sulfur, nitrogen, and oxygen, $C_1$-$C_{14}$-alkoxy, halogen, carboxy, cyano, $C_1$-$C_{14}$-alkanoyloxy, $C_1$-$C_{14}$-alkylthio, $C_1$-$C_{14}$-alkylsulfonyl, trifluoromethyl, hydroxy, $C_2$-$C_{14}$-alkoxycarbonyl, $C_2$-$C_{14}$-alkanoylamino, —O—$R^2$, S—$R^2$, —$SO_2$—$R^2$, —$NHSO_2R^2$ or —$NHCO_2R^2$; and $R^2$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen, and $C_4$-$C_{20}$ hydroxyheteroaryl wherein the heteroatom is sulfur, nitrogen, oxygen or a mixture thereof.

Another embodiment of the present invention concerns a skin brightening composition comprising and ester represented by formula 1:

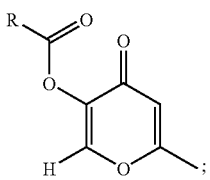

and
a dermatologically acceptable carrier,
wherein R is $C_1$-$C_{24}$ alkyl, $C_2$-$C_{24}$ alkenyl, $C_4$-$C_{24}$ dienyl, $C_6$-$C_{24}$ trienyl, $C_8$-$C_{24}$ tetraenyl, or a mixture thereof, $C_6$-$C_{14}$ aryl, substituted $C_6$-$C_{14}$ aryl, substituted and unsubstituted $C_4$-$C_{20}$ heterocyclic wherein the heteroatoms are selected from sulfur, nitrogen, and oxygen, $C_1$-$C_{14}$-alkoxy, halogen, carboxy, cyano, $C_1$-$C_{14}$-alkanoyloxy, $C_1$-$C_{14}$-alkylthio, $C_1$-$C_{14}$-alkylsulfonyl, trifluoromethyl, hydroxy, $C_2$-$C_{14}$-alkoxycarbonyl, $C_2$-$C_{14}$-alkanoylamino, —O—$R^2$, S—$R^2$, —$SO_2$—$R^2$, —$NHSO_2R^2$ or —$NHCO_2R^2$; and $R^2$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen, and $C_4$-$C_{20}$ hydroxyheteroaryl wherein the heteroatom is sulfur, nitrogen, oxygen or a mixture thereof.

Yet another embodiment concerns a method for the preparation of an ester compound represented by formula 1:

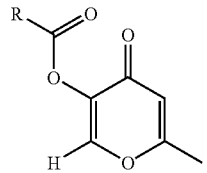

the method comprising reacting a compound represented by formula 2:

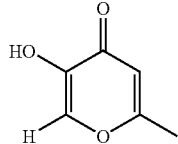

with an acid, anhydride, or acid derivative of formula 3:

to form said ester;

wherein R is $C_2$-$C_{24}$ alkyl, $C_2$-$C_{24}$ alkenyl, $C_4$-$C_{24}$ dienyl, $C_6$-$C_{24}$ trienyl, $C_8$-$C_{24}$ tetraenyl, or a mixtures thereof, $C_6$-$C_{14}$ aryl, substituted $C_6$-$C_{14}$ aryl, substituted and unsubstituted $C_4$-$C_{20}$ heterocyclic wherein the heteroatoms are selected from sulfur, nitrogen, and oxygen, $C_1$-$C_{14}$-alkoxy, halogen, carboxy, cyano, $C_1$-$C_{14}$-alkanoyloxy, $C_1$-$C_{14}$-alkylthio, $C_1$-$C_{14}$-alkylsulfonyl, trifluoromethyl, hydroxy, $C_2$-$C_{14}$-alkoxycarbonyl, $C_2$-$C_{14}$-alkanoylamino, —O—$R^2$, S—$R^2$, —$SO_2$—$R^2$, —$NHSO_2R^2$ or —$NHCO_2R^2$, $R^2$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen, and $C_4$-$C_{20}$ hydroxyheteroaryl wherein the heteroatoms are selected from the group consisting of sulfur, nitrogen, and oxygen;

R″ is —OH, —SH, —F, —Cl, —Br, —I, or —OR‴; and

R‴ is $C_{1-12}$ n-alkyl, substituted $C_{1-12}$ n-alkyl (e.g. —$CF_3$), $C_{3-12}$ branched alkyl, substituted $C_{3-12}$ branched alkyl, $C_{3-8}$ cycloalkyl, substituted $C_{3-8}$ cycloalkyl, aryl, substituted aryl (e.g. —$SO_2$—$R^2$), aralkyl or substituted aralkyl.

DETAILED DESCRIPTION

The present invention relates to esters, skin brightening compositions which employ the esters, and methods of making and using the esters. The esters according to the present invention can be represented by the following formula 1:

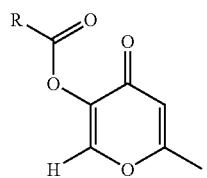

wherein R is $C_2$-$C_{24}$ alkyl, $C_2$-$C_{24}$ alkenyl, $C_4$-$C_{24}$ dienyl, $C_6$-$C_{24}$ trienyl, $C_8$-$C_{24}$ tetraenyl, or a mixture thereof, $C_6$-$C_{14}$ aryl, substituted $C_6$-$C_{14}$ aryl, substituted and unsubstituted $C_4$-$C_{20}$ heterocyclic wherein the heteroatoms are selected from sulfur, nitrogen, and oxygen, $C_1$-$C_{14}$-alkoxy, halogen, carboxy, cyano, $C_1$-$C_{14}$-alkanoyloxy, $C_1$-$C_{14}$-alkylthio, $C_1$-$C_{14}$-alkylsulfonyl, trifluoromethyl, hydroxy, $C_2$-$C_{14}$-alkoxycarbonyl, $C_2$-$C_{14}$-alkanoylamino, —O—$R^2$, S—$R^2$, —$SO_2$—$R^2$, —$NHSO_2R^2$ or —$NHCO_2R^2$; and $R^2$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen, and $C_4$-$C_{20}$ hydroxyheteroaryl wherein the heteroatom is sulfur, nitrogen, oxygen or a mixture thereof.

Another embodiment concerns skin brightening compositions based on esters represented by the following formula 1:

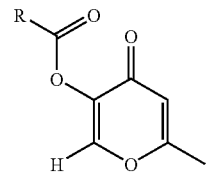

wherein R is $C_1$-$C_{24}$ alkyl, $C_2$-$C_{24}$ alkenyl, $C_4$-$C_{24}$ dienyl, $C_6$-$C_{24}$ trienyl, $C_8$-$C_{24}$ tetraenyl, or a mixture thereof, $C_6$-$C_{14}$ aryl, substituted $C_6$-$C_{14}$ aryl, substituted and unsubstituted $C_4$-$C_{20}$ heterocyclic wherein the heteroatoms are selected from sulfur, nitrogen, and oxygen, $C_1$-$C_{14}$-alkoxy, halogen, carboxy, cyano, $C_1$-$C_{14}$-alkanoyloxy, $C_1$-$C_{14}$-alkylthio, $C_1$-$C_{14}$-alkylsulfonyl, trifluoromethyl, hydroxy, $C_2$-$C_{14}$-alkoxycarbonyl, $C_2$-$C_{14}$-alkanoylamino, —O—$R^2$, S—$R^2$, —$SO_2$—$R^2$, —$NHSO_2R^2$ or —$NHCO_2R^2$; and $R^2$ is phenyl, naphthyl, or phenyl or naphthly substituted with one to three groups selected from $C_1$-$C_6$-alkyl, $C_6$-$C_{10}$ aryl, $C_1$-$C_6$-alkoxy and halogen, and $C_4$-$C_{20}$ hydroxyheteroaryl wherein the heteroatom is sulfur, nitrogen, oxygen or a mixture thereof.

In an embodiment, the esters are prepared by reacting a compound represented by formula 2:

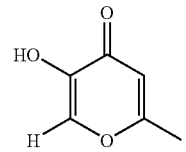

with an acid, anhydride, or acid derivative of formula 3:

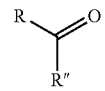

wherein R″ is —OH, —SH, —F, —Cl, —Br, —I, or —OR‴; and

R‴ is $C_{1-12}$ n-alkyl, substituted $C_{1-12}$ n-alkyl (e.g. —$CF_3$), $C_{3-12}$ branched alkyl, substituted $C_{3-12}$ branched alkyl, $C_{3-8}$ cycloalkyl, substituted $C_{3-8}$ cycloalkyl, aryl, substituted aryl (e.g. —$SO_2$—$R^2$), aralkyl or substituted aralkyl.

In an embodiment, the process comprises reacting a compound represented by formula 2 with an acid, anhydride, or acid derivative of formula 3 in the presence of an organic solvent (e.g. diethyl ether, tetrahydrofuran, methylene chloride, chloroform, etc.) or a mixed organic solvent. The reaction is typically allowed to run to completion, usually about 30 minutes. Shorter or longer reaction times may be required and can be determined by those of ordinary skill in the art. Upon completion of the reaction, the resulting ester can be isolated and purified by techniques known to those of ordinary skill in the art (e.g. flash chromatography, etc.).

The esters according to the present invention can be used in skin brightening compositions. Such compositions may also contain other skin brightening ingredients such as tetronic acid, tetronic acid derivatives, hydroquinone, kojic acid, 4-hydroxybenzyl alcohol, gallic acid, arbutin, α-hydroxyl acids, and fatty acid esters of ascorbic acid. Such other ingredients are known to those of skill in the art.

Typically, topical application to skin sites is accomplished in association with a carrier, and particularly one in which the active ingredient is soluble per se or is effectively solubilized (e.g., as an emulsion or microemulsion). Where employed, the carrier is inert in the sense of not bringing about a deactivation or oxidation of active or adjunct ingredient(s), and in the sense of not bringing about any adverse effect on the skin areas to which it is applied. For example, the compounds according to the present invention are applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin areas. While the carrier for dermatological compositions can consist of a relatively simple solvent or dispersant such as water, it is generally preferred that the carrier comprise a composition more conducive to topical application. In particular, a dermatological composition which will form a film or layer on the skin to which it is applied so as to localize the application and provide some resistance to washing off by immersion in water or by perspiration and/or aid in the percutaneous delivery of the active agent. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic, or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. Such compositions are referred to herein as dermally, dermatologically, or pharmaceutically acceptable carriers.

Suitable carriers include water, alcohols, oils and the like, chosen for their ability to dissolve or disperse ingredients used in the treatment. In some embodiments, active and/or adjunct ingredients are added to a sunscreen or sunblock formulations so that topical application has the further advantage of preventing repigmentation during and/or after treatment. Preferred formulae of this type are SPF 15 or higher. Many of these preferred embodiments contain titanium dioxide or zinc oxide which additionally soothe and lubricate the skin and help minimize side effects in sensitive skin and with formulations containing high concentrations of bleaching ingredients.

Generally in the practice of methods of the invention, the composition is topically applied to darker skin areas on a subject in a predetermined or as-needed regimen either at intervals by application of a lotion or the like, it generally being the case that gradual brightening is noted with each successive application. Insofar as has been determined based upon in vitro studies, no adverse side effects are encountered.

"Therapeutically effective amount" or "effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying or preventing the onset or reoccurrence of the disease or disorder or at least symptoms thereof in a subject which may be exposed to or predisposed to or may have previously suffered from a disease or disorder even though that subject does not yet experience or display symptoms of the disease or disorder.

Typical compositions of the invention contain from about 6.00% to about 0.01% by weight, from about 4.00% to about 0.25% by weight, from about 2.00% to about 0.50% by weight, or from about 1.50% to about 1.00% by weight of the esters according to formula 1 described above. Lower concentrations may be employed for less pronounced conditions (e.g. hyperpigmentation and in sunscreens and sunblocks used after skin brightening treatment) and higher concentrations may be employed with more acute conditions.

It should be understood that the ingredients particularly mentioned above are merely examples and that some embodiments of formulations comprising the compositions of the present invention include other suitable components and agents. The compositions of the invention may be used for, among other things, pharmaceutical and cosmetic purposes and may be formulated with different ingredients according to the desired use.

The invention further includes packages, vessels, or any other type of container that contain a 5-hydroxy-2-methyl-4H-pyran-4-one ester, blends thereof, or any composition comprising a 5-hydroxy-2-methyl-4H-pyran-4-one ester formulation of the present invention.

EXAMPLES

The processes provided by the present invention are further illustrated by the following examples.

In vitro assay: Tyrosinase catalyzes the first two biosynthetic steps in the tyrosine to melanin pathway. Tyrosinase hydroxylates tyrosine to dihydroxyphenylalanine (L-DOPA) and subsequently oxidizes L-DOPA to dopaquinone. One method to determine compound tyrosinase inhibition activity utilizes dopaquinone formation; L-DOPA oxidation forms dopaquinone and monitored at 475 nm. The enzyme assay was largely based on the method described in Zhang, J P., Chen, Q X., Song, K K., & Xie, J J. *Food Chemistry* 2006, 95, 579-584.

First, compound solubility gets evaluated in an aqueous environment and appropriate dilutions are prepared in either water or dimethyl sulfoxide. Dilutions are prepared from stock solutions, typically to measure final inhibitor concentrations ranging from 10 nM to 10 mM.

The assay mixture is composed of 50 mM $Na_2HPO_4$/$NaH_2PO_4$ pH 7.0 and 0.5 mM L-DOPA. The enzymatic reaction is commenced by addition of 18 Units of mushroom tyrosinase (Sigma T3824). A baseline initial rate of tyrosinase activity is measured at 475 nm using a Beckman Coulter DU 800 UV/Vis Spectrophotometer in 1.0 ml reaction format at 30° C., then a 25 ul aliquot of the inhibitor solution is added/mixed and the change in rate is noted. The change in rate relates to the percent inhibition of tyrosinase due to the presence of the inhibitor. Inhibitory effects of any DMSO present are minimized by limiting the final concentration to 2.5% and accounting for any background inhibition with DMSO blanks for each assay.

The degree of tyrosinase inhibition was measured in terms of the concentration of inhibitor necessary to inhibit tyrosinase by 50%, the $EC_{50}$ value. This was determined by sigmoidal dose-response curves generated in Graphpad Prizm® Version 4 by plotting the log of inhibitor concentration against the rate response (% inhibition).

It should be understood that the assay method mentioned above merely describes general procedures and that other suitable components, reagent concentrations, and/or agents and/or analytical equipment may be used.

Chemical Synthesis: The general methods to prepare 5-hydroxy-2-methyl-4H-pyran-4-one esters are illustrated below.

Synthesis of 5-hydroxy-2-methyl-4H-pyran-4-one esters

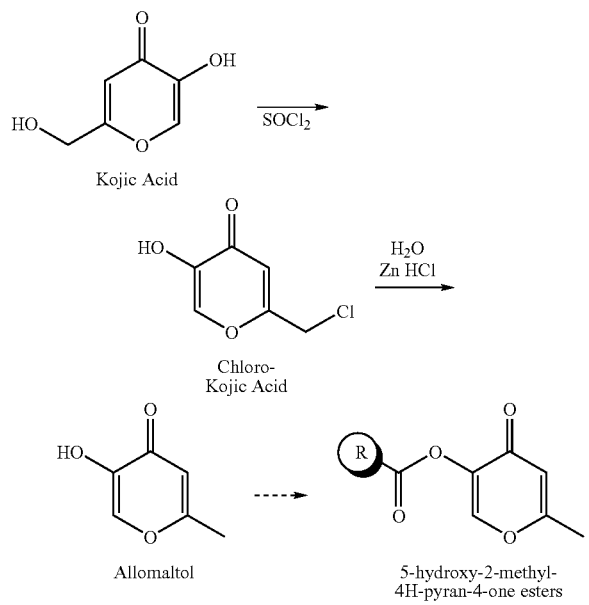

Preparation of 2-(chloromethyl)-5-hydroxy-4H-pyran-4-one (chloro-kojic acid): Kojic Acid (50.0 g; 352 mmol)—an inhibitor of tyrosinase with an $EC_{50}$ of 17.0 µM—was carefully added in portions over 30 min to a stirring solution of thionyl chloride (150 mL) containing hexanes (100 mL). After an additional 3.5 hours of stirring, the product was collected by Büchner filtration and washed with hexanes (2×50 mL). The light yellow solid was dried over night under vacuum to afford chloro-kojic acid (50.9 g; 90% yield). Chloro-kojic acid was found to be a more potent inhibitor of tyrosinase than kojic acid with an $EC_{50}$ of 6.8 µM. $^1$H NMR (DMSO-$d_6$) δ 9.30 (br s, 1H; 5-OH); 8.12 (s, 1H; 6-H); 6.56 (s, 1H; 3-H); 4.66 (s, 2H; 2-$CH_2$Cl).

Preparation of 5-hydroxy-2-methyl-4H-pyran-4-one (allomaltol): Chloro-kojic Acid (20.0 g; 125 mmol)—an inhibitor of tyrosinase with an $EC_{50}$ of 6.8 µM—was added in portions to HPLC grade water (60 mL) and heated with an oil bath to ~50° C. Zinc dust (16.2 grams) was carefully added in portions (5 min). An addition funnel was then attached. The reaction temperature was then increased to ~70° C. and concentrated HCl (37 mL) was added drop-wise over 60 min; the reaction was vigorously stirred for an additional 3 hours. Next, excess zinc was removed via hot Büchner filtration. Standard extraction and purification methods afforded allomaltol (10.3 g; 81.7 mmol; 65% yield); see Liu, Z. D. et al, *Bioorg. Med. Chem.* 2001, 9, 563-573. Allomaltol was found to be a more potent inhibitor of tyrosinase than kojic acid with an $EC_{50}$ of 3.4 µM. $^1$H NMR (DMSO-$d_5$) δ 9.3-8.3 (br s, 1H; 5-OH); 7.97 (s, 1H; 6-H); 6.23 (s, 1H; 3-H); 2.24 (s, 3H; 2-$CH_3$).

Preparation of 6-methyl-4-oxo-4H-pyran-3-yl acetate: Allomaltol (600 mg; 4.76 mmol) was weighed out into a round bottom flask (100 ml) containing a stir-bar. The contents were diluted with anhydrous THF (~20 ml) and stirred (~5 min) to afford a solution. Next, trimethyl amine (833 µl; 6.33 mmol; 1.33 equiv.) was added drop-wise and the contents stirred (~5 min). Acetic anhydride (641 µl; 5.00 mmol) was then added drop-wise, capped and stirred at room temperature. The reaction was monitored via silica gel TLC. Once complete, the reaction mixture was concentrated under reduced pressure and the contents purified by silica gel chromatography to afford 650 mg product (3.87 mmol; 81% yield). This compound was found to have an $EC_{50}$ of 106 µM. $^1$H NMR (DMSO-$d_6$) δ 8.39 (s, 1H; 2-H); 6.36 (s, 1H; 5-H); 2.30 (s, 3H); 2.24 (s, 3H).

Preparation of 6-methyl-4-oxo-4H-pyran-3-yl propanoate: Allomaltol (600 mg; 4.76 mmol) was weighed out into a round bottom flask (100 ml) containing a stir-bar. The contents were diluted with anhydrous THF (~20 ml) and stirred (~5 min) to afford a solution. Next, trimethyl amine (833 µl; 6.33 mmol; 1.33 equiv.) was added drop-wise and the contents stirred (~5 min). Propionic anhydride (473 µl; 5.00 mmol) was then added drop-wise, capped and stirred at room temperature. The reaction was monitored via silica gel TLC. Once complete, the reaction mixture was concentrated under reduced pressure and the contents purified by silica gel chromatography to afford (680 mg product; 3.73 mmol; 78% yield). This compound was found to have an $EC_{50}$ of 620 µM. $^1$H NMR (DMSO-$d_6$) δ 8.39 (s, 1H; 2-H); 6.36 (s, 1H; 5-H); 2.59-2.55 (q, 2H; —$CH_2$—); 2.29 (s, 3H; 6-$CH_3$); 1.13-1.08 (t, 3H; —$CH_3$).

Preparation of 6-methyl-4-oxo-4H-pyran-3 yl hexanoate: Allomaltol (600 mg; 4.76 mmol) was weighed out into a round bottom flask (100 ml) containing a stir-bar. The contents were diluted with anhydrous THF (~20 ml) and stirred (~5 min) to afford a solution. Next, trimethyl amine (833 µl; 6.33 mmol; 1.33 equiv.) was added drop-wise and the contents stirred (~5 min). Hexanoic anhydride (1030 µl; 954 mg; 4.45 mmol) was then added drop-wise, capped and stirred at room temperature. The reaction was monitored via silica gel TLC. Once complete, the reaction mixture was concentrated under reduced pressure and the contents purified by silica gel chromatography to afford 760 mg of light yellow crystalline product (3.39 mmol; 76% yield). This compound was found to have an $EC_{50}$ of 354 µM. $^1$H NMR (DMSO-$d_6$) δ 8.39 (s, 1H; 2-H); 6.35 (s, 1H; 5-H); 2.54-2.52 (t, 2H); 2.29 (s, 3H; 6-CH₃); 1.62-1.58 (p, 2H); 1.35-1.24 (m, 4H); 0.89-0.86 (t, 3H; —CH₃).

Preparation of 6-methyl-4-oxo-4H-pyran-3-yl octanoate: Allomaltol (600 mg; 4.76 mmol) was weighed out into a round bottom flask (100 ml) containing a stir-bar. The contents were diluted with anhydrous THF (~20 ml) and stirred (~5 min) to afford a solution. Next, trimethyl amine (833 μl; 6.33 mmol; 1.33 equiv.) was added drop-wise and the contents stirred (~5 min). Octanoyl chloride (770 μl; 724 mg; 4.45 mmol) was then added drop-wise, capped and stirred at room temperature. The reaction was monitored via silica gel TLC. Once complete, the reaction mixture was concentrated under reduced pressure and the contents purified by silica gel chromatography to afford 1.01 g of light yellow crystalline product (4.00 mmol; 90% yield). This compound was found to have an $EC_{50}$ of 532 μM. ¹H NMR (DMSO-d₆) δ 8.39 (s, 1H; 2-H); 6.35 (s, 1H; 5-H); 2.54-2.52 (t, 2H); 2.29 (s, 3H; 6-CH₃); 1.60-1.58 (p, 2H); 1.34-1.31 (m, 2H); 1.31-1.24 (m, 6H); 0.87-0.85 (t, 3H; —CH₃).

Preparation of 6-methyl-4-oxo-4H-pyran-3-yl benzoate: Allomaltol (600 mg; 4.76 mmol) was weighed out into a round bottom flask (100 ml) containing a stir-bar. The contents were diluted with anhydrous THF (~20 ml) and stirred (~5 min) to afford a solution. Next, trimethyl amine (833 μl; 6.33 mmol; 1.33 equiv.) was added drop-wise and the contents stirred (~5 min). Benzoyl chloride (517 μl; 627 mg; 4.46 mmol) was then added drop-wise, capped and stirred at room temperature. The reaction was monitored via silica gel TLC. Once complete, the reaction mixture was concentrated under reduced pressure and the contents purified by silica gel chromatography to afford 930 mg of light yellow crystalline product (4.04 mmol; 91% yield). This compound was found to have an $EC_{50}$ of >1 mM. ¹H NMR (DMSO-d₆) δ 8.58 (s, 1H; 2-H); 8.09-8.07 (dd, 2H); 7.78-7.76 (t, 1H); 7.63-7.59 (t, 2H); 6.43 (s, 1H; 5-H); 2.34 (s, –3H; 6-CH₃).

Preparation of 6-methyl-4-oxo-4H-pyran-3-yl 4-fluorobenzoate: Allomaltol (600 mg; 4.76 mmol) was weighed out into a round bottom flask (100 ml) containing a stir-bar. The contents were diluted with anhydrous THF (~20 ml) and stirred (~5 min) to afford a solution. Next, trimethyl amine (840 μl) was added drop-wise and the contents stirred (~5 min). 4-Fluorobenzoyl chloride (600 μl) was then added drop-wise, capped and stirred at room temperature. The reaction was monitored via silica gel TLC. Once complete, the reaction mixture was concentrated under reduced pressure and the contents purified by silica gel chromatography to afford 1.04 g crystalline product (4.19 mmol; 88% yield). This compound was found to have an $EC_{50}$ of >1 mM. ¹H NMR (DMSO-d₆) δ 8.59 (s, 1H; 2-H); 8.18-8.13 (dd, 2H); 7.47-7.41 (t, 2H); 6.44 (s, 1H; 5-H); 2.34 (s, –3H; 6-CH₃).

Preparation of 6-methyl-4-oxo-4H-pyran-3 yl nicotinate: Allomaltol (1.266 g, 10 mmol) was dissolved in 40 mL of anhydrous THF. The mixture was cooled to 0° C. Triethylamine (1.8 mL, 13 mmol) was added. Nicotinoyl chloride hydrochloride (1.988 g, 11 mmol) was added portionwise. Cold bath was removed and the mixture was stirred at room temperature overnight. The reaction was neutralized with ammonia hydroxide then extracted with EtOAc. The organic phase was washed with brine 2 times then dried over Na₂SO₄ and concentrated. The crude product was purified with flash chromatography using DCM/MeOH to give the desired product as an off-white solid (1.35 g, 58%). MP (148° C.). ¹H NMR (CDCl₃) δ (ppm): 2.27 (d, 3H, J=0.9 Hz), 6.26 (d, 1H, J=0.9 Hz), 7.42 (dd, 1H, J=4.8, 8.1 Hz), 7.95 (s, 1H), 8.37 (td, 1H, J=1.8, 7.8 Hz), 8.79 (br s, 1H), 9.28 (br s, 1H). ¹³C NMR (CDCl₃) δ (ppm): 19.8, 115.3, 123.8, 124.7, 138.2, 140.8, 148.1, 151.3, 154.1, 162.4, 166.4, 172.4.

Preparation of 6-methyl-4-oxo-4H-pyran-3 yl furan-2-carboxylate: Allomaltol (1.256 g, 10 mmol) was dissolved in 40 mL of anhydrous THF. The mixture was cooled to 0° C. Triethylamine (1.8 mL, 13 mmol) was added. Furan-2-carbonyl chloride (1.500 g, 11 mmol) was added dropwise. Cold bath was removed and the mixture was stirred at room temperature overnight. The reaction was extracted with EtOAc. The organic phase was washed with brine 2 times then dried over Na₂SO₄ and concentrated. The crude product was purified with flash chromatography using EtOAc/hexanes to give the desired product as a brown solid (1.539 g, 70%). MP (136° C.). ¹H NMR (CDCl₃) δ (ppm): 2.30 (s, 3H), 6.29 (s, 1H), 6.55 (m, 1H), 7.37 (m, 1H), 7.64 (m, 1H), 7.94, (s, 1H). ¹³C NMR (CDCl₃) δ (ppm): 19.8, 112.6, 115.4, 120.8, 140.5, 143.0, 147.9, 148.4, 155.4, 166.5, 172.1.

The invention has been described in detail with particular reference to preferred embodiments thereof, but it will be understood that variations and modifications can be effected within the spirit and scope of the invention.

We claim:

1. An ester represented by formula 1:

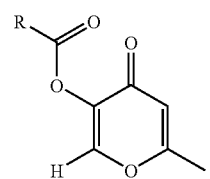

wherein R is selected from the group consisting of substituted and unsubstituted $C_4$-$C_{20}$ heteroaryl wherein the heteroatoms are selected from sulfur, nitrogen, and oxygen.

2. A skin brightening composition comprising an ester represented by formula 1:

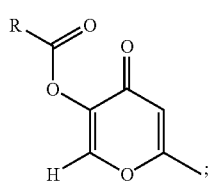

and
a dermatologically acceptable carrier,
wherein R is substituted and unsubstituted $C_4$-$C_{20}$ heteroaryl wherein the heteroatoms are selected from sulfur, nitrogen, and oxygen.

3. The composition according to claim 2, wherein said ester is selected from the group consisting of 6-methyl-4-oxo-4H-pyran-3-yl-nicotinate and 6-methyl-4-oxo-4H-pyran furan-2-carboxylate and is present in an amount of from about 6.00% to about 0.01% by weight.

4. The composition according to claim 3, wherein said ester is present in an amount of from about 4.0% to about 0.10% by weight.

5. The composition according to claim 4, wherein said ester is present in an amount of from about 2.0% to about 0.50% by weight.

6. A method of brightening skin, comprising applying the composition according to claim 2 to skin.

7. The method according to claim 6, wherein said composition is applied to skin in a predetermined regimen or in an as-needed regimen until a desired level of skin brightening is achieve, and wherein the ester is selected from the group consisting of 6-methyl-4-oxo-4H-pyran-3-yl-nicotinate and 6-methyl-4-oxo-4H-pyran furan-2-carboxylate.

8. A method for the preparation of an ester compound represented by formula 1:

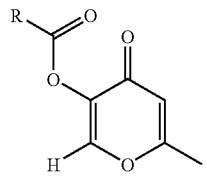

the method comprising reacting a compound represented by formula 2:

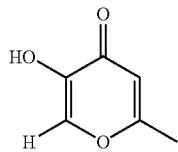

with an acid, anhydride, or acid derivative of formula 3:

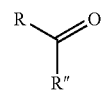

to form said ester;
wherein R is selected from the group consisting of substituted and unsubstituted $C_4$-$C_{20}$ heteroaryl wherein the heteroatoms are selected from sulfur, nitrogen, and oxygen;
R″ is —OH, —SH, —F, —Cl, —Br, —I, or —OR‴; and
R‴ is $C_{1-12}$ n-alkyl, substituted $C_{1-12}$ n-alkyl, $C_{3-12}$ branched alkyl, substituted $C_{3-12}$ branched alkyl, $C_{3-8}$ cycloalkyl, substituted $C_{3-8}$ cycloalkyl, aryl, substituted aryl, aralkyl or substituted aralkyl.

9. A skin brightening composition comprising 6-methyl-4-oxo-4H-pyran-3-yl-nicotinate and a dermatologically acceptable carrier, wherein said 6-methyl-4-oxo-4H-pyran-3-yl-nicotinate is present in an amount of from about 6.00% to about 0.01% by weight.

* * * * *